(12) United States Patent
Shi et al.

(10) Patent No.: US 10,443,080 B2
(45) Date of Patent: Oct. 15, 2019

(54) STARCH SPHERULITES HAVING CONTROLLED ENZYMATIC DIGESTION

(71) Applicant: Kansas State University Research Foundation, Manhattan, KS (US)

(72) Inventors: Yong-Cheng Shi, Manhattan, KS (US); Liming Cai, Atchison, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 125 days.

(21) Appl. No.: 14/714,457

(22) Filed: May 18, 2015

(65) Prior Publication Data

US 2015/0247176 A1    Sep. 3, 2015

Related U.S. Application Data

(63) Continuation-in-part of application No. PCT/US2013/070968, filed on Nov. 20, 2013.

(60) Provisional application No. 61/728,513, filed on Nov. 20, 2012.

(51) Int. Cl.

| | |
|---|---|
| *C12P 19/16* | (2006.01) |
| *C12P 19/04* | (2006.01) |
| *A61K 47/36* | (2006.01) |
| *C08B 30/18* | (2006.01) |
| *C08B 37/00* | (2006.01) |
| *C08J 3/12* | (2006.01) |
| *C08L 3/02* | (2006.01) |
| *C08L 5/00* | (2006.01) |
| *C12P 19/14* | (2006.01) |
| *A23L 29/30* | (2016.01) |

(52) U.S. Cl.
CPC .............. *C12P 19/16* (2013.01); *A23L 29/35* (2016.08); *A61K 47/36* (2013.01); *C08B 30/18* (2013.01); *C08B 37/0009* (2013.01); *C08J 3/12* (2013.01); *C08L 3/02* (2013.01); *C08L 5/00* (2013.01); *C12P 19/04* (2013.01); *C12P 19/14* (2013.01); *C08J 2303/02* (2013.01); *C08J 2305/00* (2013.01); *C12Y 302/01041* (2013.01); *C12Y 302/01068* (2013.01)

(58) Field of Classification Search
CPC ........ G01S 19/05; G01S 5/0072; A23L 29/35; A61K 47/36; C08B 30/18; C08B 37/0009; C08J 2303/02; C08J 2305/00; C08J 3/12; C08L 3/02; C08L 5/00; C12P 19/04; C12P 19/14; C12P 19/16; C12Y 302/01041; C12Y 302/01068

See application file for complete search history.

(56) References Cited

U.S. PATENT DOCUMENTS 7,754,017 B2   7/2010   Stanley et al.
7,833,356 B2   11/2010  Woortman et al.

OTHER PUBLICATIONS

Ziegler et al. (2005) biomacromolecules 6: 1547-1554.*
Hii et al. (2012) Enzyme Research 2012: 1-14.*
Singh et al. (2010) Food Chemistry 121: 980-989.*
Guraya et al. (2001) STarch 53: 131-139. (Year: 2001).*
Xie et al. (2014) International Journal of Biological Macromolecules 67: 79-84. (Year: 2014).*
Cai, Liming, "Self-Assembly of Short Linear Chains to A- and B-Type Starch Spherulites and Their Enzymatic Digestibility" Journal of Agricultural and Food Chemistry, Oct. 7, 2013, pp. 10787-10797, vol. 61, American Chemical Society.
Creek, John A. "Amylose Crystallization from Concentrated Aqueous Solution," Biomacromolecules, Feb. 23, 2006, pp. 761-770, vol. 7, American Chemical Society.
Nordmark, Tor S. "Spherulitic Crystallization of Gelatinized Maize Starch and its Fractions," Carbihydrate Polymers, 2002, pp. 439-448, vol. 49, Elsevier Science Ltd.
Singh, Jaspreet, "Formation of Starch Spherulites: Role of Amylose Content and Thermal Events," Food Chemistry, Jan. 21, 2010, pp. 980-989, vol. 121, Elsevier Science Ltd.
Ziegler, Gregory, "Spherulitic Crystallization of Starch: Influence of Botanical Origin and Extent of Thermal Treatment," Food Hydrocolloids, 2003 pp. 487-494, vol. 17, Elsevier Science Ltd.
Ziegler, Gregory, "Spherulitic Crystallization in Starch as a Model for Starch Granule Initiation," Biomacromolecules, Mar. 25, 2005, pp. 1547-1554, vol. 6, American Chemical Society.
International Search Report and Written Opinion dated Mar. 17, 2014, in the PCT/US2013/070968 filed Nov. 20, 2013.
Gidley, Michael J. "Factors Affecting the Crystalline Type (A-C) of Native Starches and Model Compounds: a Rationalisation of Observed Effects in Terms of Polymorphic Structures," Carbohydrate Research, 1987, pp. 301-304. vol. 161, Elsevier Science Publishers B.V., Amsterdam.
Sang, Yijun, "Resistant Starches from Amylose Mutants of Corn by Simultaneous Heat-Moisture Treatment and Phosphorylation," Carbohydrate Polymers, Dec. 15, 2005, pp. 167-175, vol. 63, Elsevier Ltd.
Cai, Liming, "Structure and Digestibility of Crystalline Short-Chain Amylose from Debranched Waxy Wheat, Waxy Maize, and Waxy Potato Starches," Carbohydrate Polymers, 2010, pp. 1117-1123, vol. 79, Elsevier Ltd.
Cai, Liming, "Debranching and Crystallization of Waxy Maize Starch in Relation to Enzyme Digestibility," Carbohydrate Polymers, 2010, pp. 385-393, vol. 81. Elsevier Ltd.
Wang, Shujin, "New Insights on the Mechanism of Acid Degradation of Pea Starch," Carbohydrate Polymers, 2012, pp. 1941-1949, vol. 87, Elsevier Ltd.

(Continued)

*Primary Examiner* — Lisa J Hobbs
(74) *Attorney, Agent, or Firm* — Hovey Williams LLP (57) ABSTRACT

Starch spherulites are produced by debranching of amylopectin-containing starch into short linear α-1,4-linked glucans (e.g., short-chain amylose, SCA). The debranched linear glucans are directly converted into spherulites by heating the debranched starch mixture followed by cooling and crystallization to form well-developed spherulites. The spherulites exhibit controlled enzyme digestibility.

10 Claims, 9 Drawing Sheets

(56) References Cited

OTHER PUBLICATIONS

Englyst, H. H. "Classification and Measurement pf Nutritionally Important Starch Fractions," European Journal of Clinical Nutrition, 1992, pp. 33-50, vol. 46 (Suppl. 2), Macmillan Press Ltd.
Jenkins, Paul J., "The Effect of Acid Hydrolyis on Native Starch Granule Structure," Starch/Starke, 1997, pp. 262-267, vol. 49, Wiley-VCH Verlag GmbH, D-69451 Weinheim.

* cited by examiner

STARCH SPHERULITES HAVING CONTROLLED ENZYMATIC DIGESTION

RELATED APPLICATIONS

The present application is a continuation-in-part of International Patent Application No. PCT/US13/70968, filed Nov. 20, 2013, which claims the benefit of U.S. Provisional Patent Application No. 61/728,513, filed Nov. 20, 2012, both of which are incorporated by reference herein in their entireties.

BACKGROUND OF THE INVENTION

Field of the Invention

The present invention is generally directed toward a process combining enzymatic debranching, melting, and crystallization to produce spherulites from linear α-1,4-linked glucans (e.g., short-chain amylose, SCA) with controlled enzyme digestibility. The linear α-1,4-linked glucans can be obtained by debranching starch, heating the mixture followed by cooling and crystallization to form well-developed spherulites.

Description of the Prior Art

Spherulites are important structural features found in many polymers crystallized from a melt. Starch-based spherulites may be obtained by cooling the starch suspension preheated into a solution state without disturbance. The overall morphology of spherulites is dependent on starch sources, amylose content, and crystallization conditions such as heating temperature, concentration of starting materials, cooling rate, and crystallization temperature. High-amylose starches form spherical structures with birefringence more readily than normal and waxy starches. Spherulites may form over a wide range of cooling rates (1-250° C./min) provided that amylose solution (10 to 20%, w/w) was preheated to greater than 170° C. Spherulitic crystals display dimensions and structural characteristics consistent with the hilum and core region of native granules, thus have been proposed as a model for starch granule initiation in vivo; however, in those studies, amylose was isolated from granular starch by an aqueous leaching process, and the spherulites were prepared in a differential scanning calorimetry (DSC) pan. A small sample size was used and was not enough for conducting digestion study.

Spherulitic crystallization from acid hydrolyzed potato starch solution has been documented as well. Helbert et al., Morphological and structural features of amylose spherocrystals of A-type. *Intern. J. Biol. Macromol.* 1993, 15, 183-187, prepared spherulites by mixing ethanol with hot aqueous solutions of low molecular weight amylose followed by slow cooling to 4° C. The precipitates had a diameter of the order of 10 μm and exhibited an A-type X-ray diffraction pattern. In contrast, spherulites with a B-type polymorph and a dimension of 10-15 μm were produced by direct cooling 5-20% w/w aqueous acid hydrolyzed potato starch solution to 2° C. Ring et al., Spherulitic crystallization of short chain amylose. *Intern. J. Biol. Macromol.* 1987, 9, 158-160. Because A- and B-amylose spherulites mimic both granular morphology and the crystalline types of native starches, they were used as model systems to study the enzymatic hydrolysis of starch crystallites. Planchot et al., Enzymatic hydrolysis of α-glucan crystallites. *Carbohydr. Res.* 1997, 298, 319-326, and Williamson et al., Hydrolysis of A-type and B-type crystalline polymorphs of starch by alpha-amylase, beta-amylase and glucoamylase-1. *Carbohydr. Polym.* 1992, 18, 179-187. The materials those authors used to prepare spherulites were obtained by extensive acid hydrolysis of native starches with hydrochloric acid. Significant loss of starch occurred during acid treatment since washing was needed to remove water-soluble products and recover acid resistant products. The product also presumably still contained branched points.

SUMMARY OF THE INVENTION

According to one embodiment of the present invention there is provided a method of producing spherulites comprising linear α-1,4-linked glucans. The method comprises providing starch comprising amylopectin. The starch is treated with one or more enzymes thereby causing debranching of the amylopectin and resulting in the creation of a starch mixture having greater than 50% α-1,4-linked glucans by weight based upon the total starch weight. The starch mixture is heated to a temperature above the melting point of the starch contained therein. The starch mixture is cooled to a temperature of between about 0° C. to about 75° C. thereby forming the spherulites.

According to another embodiment of the present invention there is provided spherulites comprising linear α-1,4-linked glucans. In particular embodiments, the spherulites comprise greater than 90% by weight of linear α-1,4-linked glucans. In other embodiments, the spherulites have an average particle size of between about 1 to about 25 μm.

According to yet another embodiment of the present invention there is provided a food product comprising the spherulites according to any embodiment of the invention described herein.

According to still another embodiment of the present invention there is provided a pharmaceutical or nutriceutical composition comprising the spherulites according to any embodiment of the invention described herein.

According to a further embodiment of the present invention there is provided a controlled-release composition comprising the spherulites according to any embodiment of the present invention described herein.

DETAILED DESCRIPTION OF THE PREFERRED EMBODIMENT

In certain embodiments of the present invention, linear α-1,4-linked glucans (e.g., short-chain amylose (SCA)) is produced by debranching of starch materials, especially amylopectin-containing starch materials (e.g., waxy maize starch), and directly converted into spherulites. As used herein, the term "spherulites" refers to small, spheroidal bodies of radiating polysaccharide crystals. The spherulites produced may be highly crystalline, generally water insoluble, have relatively high melting temperatures, and are resistant to digestion. Generally, spherulites according to the present invention crystallized at low temperatures (e.g., 25° C. or below) exhibit relatively larger particle sizes (e.g., 5-10 µm), a B-type starch X-ray diffraction pattern, lower melting temperatures (e.g., 70-110° C.), and a higher digestibility. Spherulites according to the present invention crystallized at 50° C. had relatively smaller particle sizes (e.g., 1-5 µm), an A-type diffraction pattern, higher melting temperatures (e.g., 100-140° C.), and a lower digestibility.

The native starch sources for use with certain embodiments of the present invention can be derived from any starch sources, such as waxy and non-waxy starches from wheat, maize, potato, tapioca, rice, sorghum, soybeans, chickpeas and the like. The native starch sources can be derived from high-amylose starches (greater than 40% amylose). In particular embodiments, the starch source has an amylopectin content of greater than 50% by weight, greater than 60% by weight, greater than 75% by weight, or greater than 90% by weight. In these embodiments, the starch source is a highly branched form of starch. It is also recognized that the starch may comprise slightly branched amylose molecules in addition to the highly branched amylopectin molecules. However, it is preferable that the starch spherulites produced be comprised primarily of short linear chains. Therefore, the native starch source may undergo an enzymatic debranching process in order to generate the desired linear chains. In certain embodiments, the debranching process results in the formation of completely linear chains.

In one embodiment of the invention starch is treated with isoamylase, pullalanase or other debranching enzymes, in order to produce debranched linear chains. In certain embodiments, the starch source is slurried in a buffered aqueous solution (e.g., acetate buffer) having a pH of between about 2 to about 7, between about 3 to about 6, or about 4 to 5. In certain embodiments, the level of starch in the slurry is between about 1% to about 50% by weight, or between about 5% to about 40% by weight, or between about 15% to about 30% by weight. The slurry is then heated to a temperature of between about 80° C. to about 150° C., between about 100° C. to about 140° C., or between about 110° C. to about 130° C., for a period of time of between 5 minutes to about 2 hours, between about 10 minutes to about 1 hour, or between about 15 minutes to about 45 minutes. After heating, the starch slurry is cooled to a temperature of between about 35° C. to about 75° C., between about 40° C. to about 65° C., or between about 45° C. to about 55° C. One or more starch debranching enzymes is added to the starch slurry at a level of between about 0.1% to about 5% by weight, between about 0.25% to about 5% by weight or between about 0.5% to about 2% by weight, based on the dry weight of the starch present in the slurry. The debranching operation is then continued under elevated temperature conditions for a sufficient amount of time to achieve the desired level of debranching. In certain embodiments, the debranching operation is permitted to continue for between about 1 hour to about 2 days, between about 10 hours to about 36 hours, or between about 18 hours to about 30 hours. In particular embodiments, the enzyme debranching step results in the creation of a starch mixture having an amylose content of greater than 50% by weight, greater than 90% by weight, or greater than 99% by weight based upon the total starch weight present in the mixture. In other embodiments, the starch mixture following debranching may still comprise some amylopectin; however, generally, the amylose levels will be considerably greater than the amylopectin levels.

Following debranching, the starch mixture is heated to temperature above the melting point of the starch. In certain embodiments, the heated slurry comprises less than 10% by weight alcohol (e.g., ethanol, methanol or isopropanol), less than 5% by weight alcohol, less than 1% by weight alcohol, or the slurry is substantially alcohol-free. In particular embodiments, the heating step comprises heating said SCA-containing mixture to a temperature of between about 140° C. to about 210° C., between about 160° C. to about 200° C., or between about 170° C. to about 190° C. In certain embodiments, this heating step is performed in the absence of alcohol in the starch solution. In further embodiments of the present invention, the heating step can be directly performed on the debranched starch slurry without need for an intervening washing or starch recovery step (e.g., evaporation, filtration, or the like). Thus, not only is time and energy saved, but overall spherulite yield is maximized as loss of starch due to washing or separation steps is avoided.

After this heating step, the starch mixture is cooled thereby forming the spherulites. In certain embodiments, the starch mixture is cooled to a temperature of between about 0° C. to about 75° C., between about 15° C. to about 60° C., or between about 25° C. to about 50° C. As illustrated in the Examples below, the temperature at which crystallization occurs appears to affect the thermal and other physical characteristics of the spherulites. The spherulites, once formed, may be recovered from the starch mixture such as through filtration followed by drying, or any other means know to those of skill in the art.

According to certain embodiments of the present invention, the spherulites are generally characterized by relatively small particle size. In particular embodiments, the spherulites have an average particle size of between about 1 to about 25 µm, between about 3 to about 20 µm, or between about 5 to about 15 µm.

In certain embodiments of the present invention, the spherulites comprise greater than 50% α-1,4-linked glucans by weight greater than 90% α-1,4-linked glucans by weight, or greater than 99% α-1,4-linked glucans by weight.

In certain embodiments of the present invention the amylose comprising the spherulites may have varying chain lengths. In particular embodiments, the spherulites comprise amylose molecules having a degree of polymerization of between about 10 to about 100, between about 15 to about 70, or between about 20 to about 60. Also, the degree of polymerization has an affect on the molecular weight of the amylose molecules. In certain embodiments, the amylose molecules comprising the spherulites have an average molecular weight of less than 200,000, between about 2,000 to about 20,000, or between about 3,000 to about 10,000.

As previously noted, the conditions under which the linear α-1,4-linked glucans crystallize when forming the spherulites affects certain thermal and physical characteristics of the resulting spherulites. Because the individual crystals comprising the spherulites may not necessarily be uniform, various thermal characteristics of the spherulites, such as melting temperature, may occur over a range of temperatures, rather than a single particular point. The onset point ($T_o$) is generally considered the "official" start of the melt as liquid clearly appears for the first time as a separate phase in coexistence with the crystals. The melting peak temperature ($T_p$) represents the maximum endothermic event in the melting process. The conclusory or crystallization temperature ($T_c$) is the temperature at which melting is completed, or the temperature at which recrystallization would begin. In certain embodiments, the $T_o$ of the spherulites is between about 65° C. to about 120° C., or between about 70° C. to about 110° C., or between about 95° C. to about 105° C. In certain embodiments, the $T_p$ of the spherulites is between about 70° C. to about 130° C., or between about 80° C. to about 125° C., or between about 90° C. to about 120° C. In certain embodiments, the $T_c$ of the spherulites is between about 80° C. to about 160° C., between about 90° C. to about 150° C., or between about 100° C. to about 140° C. It is understood that any of the foregoing temperatures may be used to define a particular melting point range for the spherulites of the present invention.

The spherulites made in accordance with the present invention may comprise A-type or B-type polymorphs, or a combination thereof, as determined by X-ray diffraction. Typically, A-type starch chains are crystallized in a monoclinic lattice, whereas B-type starch chains are crystallized in a hexagonal lattice. In certain embodiments of the present invention, the spherulites may comprise predominantly the A-type polymorph. In particular embodiments, the spherulites may comprise essentially all the A-type polymorph.

One embodiment of the invention comprises starch spherulites wherein the digestibility of the spherulites by amylase is reduced when compared to native (untreated) starch. In one embodiment of the invention the digestibility is controlled; meaning that the digestibility indicates sustained release of the starch. Resistant starch (RS) has been classified into five different types: Type I results from the starch being physically inaccessible to alpha-amylase (e.g. starch embedded in a protein or fiber matrix, such as found in whole grain); Type II is intact, native starch granules that as uncooked starch has a physical structure that is digestive resistant, but after gelatinization upon cooking is digestible; Type III is starch that has been cooked and gelatinized, or otherwise the native structure has been destroyed, and the starch molecules have re-associated themselves during the processing so that the starch is alpha-amylase resistant after cooking; Type IV is a result of starch chemical modification which interferes with alpha-amylase digestion; and Type V is starch-lipid complex or amylose-lipid complex. In certain embodiments of the present invention, the spherulites are of the Type III class and resistant to enzyme digestion, exhibiting less than 30% digestion, less than 20% digestion, or less than 15% digestion when exposed to an α-amylase-containing solution for 3 hours at 37° C. In particular embodiments, intact spherulites along with small fragments are observed after digestion with a mixture of α-amylase and amyloglucosidase, indicating that digestion is not homogenous and preferentially occurs in weak spherulites. A second exposure of the undigested residues to the amylases shows a similar digestive pattern as with the parent spherulites, suggesting that the spherulites are hydrolyzed by enzymes at essentially a constant digestion rate over the course of 20 min and 3 hours.

This resistance to digestion makes the spherulites of the present invention useful in the formulation of a variety of products. In one embodiment, the starch spherulites can be used as an ingredient in food products. One embodiment of the invention provides a food product comprising the spherulites of the present invention. Food products comprising the spherulites generally have reduced digestibility when compared to the food product containing the non-modified starch.

In other embodiments, the starch spherulites can be used in the pharmaceutical or supplement industry as a binder for tablets or pills. One embodiment of the invention provides a tablet or pill wherein the coating of the pill or tablet comprises the starch spherulites as described above. In a particular embodiment, the active ingredient in the tablet or pill is released more slowly than from a tablet or pill without the coating. In still other embodiments, the starch spherulites can be used in the formulation of controlled release compositions. For example, the spherulites may comprise one ingredient of a mixture or matrix that can be used to control the release of chemicals, proteins, peptides, and the like from the mixture or matrix.

In certain embodiments of the present invention, the starch spherulites are substantially insoluble in water (at 25° C.) and do not form at gel at a concentration of 10% solids in water (at a temperature of between 15-30° C.).

EXAMPLES

The following examples describe various spherulites, particularly SCA spherulites, and methods for producing the same according to certain embodiments of the present invention. It is to be understood, however, that these examples are provided by way of illustration and nothing therein should be taken as a limitation upon the overall scope of the invention.

Materials and Methods

Waxy maize starch was obtained from National Starch LLC (Bridgewater, N.J., USA), and isoamylase (EC 3.2.1.68) was obtained from Hayashibara Biochemical Laboratories, Inc. (Okayama, Japan). The enzyme activity of isoamylase was $1.41 \times 10^6$ isoamylase activity units (IAU)/g as determined by incubating the enzyme with soluble waxy maize starch as a substrate in the presence of iodine for 30 min under the assay conditions (pH=3.5, 40.0±0.1° C.). One IAU was defined as the amount of isoamylase that increased absorbance of the reaction mixture by 0.008 in 30 min. All chemicals were reagent-grade.

Debranching of Starch and Formation of Spherulites

Waxy maize starch (25 g, dry basis) was slurried in an acetate buffer (75 ml, 0.01M, pH 4.0) in a pressure bottle (Ace Glass Incorporated, Vineland, N.J., USA). The slurry was heated in a boiling water bath with continuous stirring for 30 min, then held at 120° C. in an oven for 30 min. After the mixture was cooled to 50° C., 1 wt. % isoamylase based on the dry weight of starch was added and the mixture was stirred at 50° C. for 24 h. The debranched starch molecules were confirmed to be linear. Three portions (15 mL each) of the mixture were sealed in pressure tubes (Ace Glass Incorporated, Vineland, N.J., USA) followed by heating in an oven at 180° C. for 20 min. The individual tubes were stored at 4, 25, or 50° C. for 24 h. The precipitate in a tube was filtered, washed with water, dried at 40° C. in an oven overnight, and ground by a mortar and pestle gently. To determine the optimum heating temperature required to form spherulites, two other portions of the mixture (15 mL each) were sealed and heated to 170 and 190° C. for 20 min, respectively, then crystallized at 4° C. for 24 h.

To determine the yield of spherulites, a mixture containing the crystals was centrifuged (×13,226 g) for 10 min and an aliquot (1.0 mL) of the supernatant was analyzed for the soluble carbohydrate with a portable refractometer (Fisher Scientific Inc., Pittsburgh, Pa., USA). The blank reading was determined by the same procedure on uncooked starch slurry that contained isoamylase. The level of precipitation of carbohydrate was calculated by the difference between refractive index measurement on a sample and the blank. Each measurement was done in duplicate.

Gel Permeation Chromatography (GPC)

The molecular size distribution of chains in spherulites was examined by GPC as described in Cai et al., Structure and digestibility of crystalline short-chain amylose from debranched waxy wheat, waxy maize and waxy potato starches, *Carbohydr. Polym.* 2010, 79, 1117-1123, and Cai et al., Debranching and crystallization of waxy maize starch in relation to enzyme digestibility, *Carbohydr. Polym.* 2010, 81, 385-393, both of which are incorporated by reference herein in their entireties. A starch sample (4 mg) was stirred with dimethyl sulfoxide (DMSO) (4 mL) in a boiling water bath for 24 h, then filtered through a 2 μm filter and injected by an autosampler into a PL-GPC 220 system (Polymer Laboratories Inc., Amherst, Mass., USA) with three Phenogel columns (00H-0642-K0; 00H-0644-K0; OOH-0646-K0; Phenomenex Inc., Torrance, Calif., USA), one guard column (03B-0290-K0, Phenomenex Inc., Torrance, Calif., USA), and a differential refractive index detector. The eluting solvent was DMSO containing 0.5 mM $NaNO_3$, and the flow rate was 0.8 mL/min. The column oven temperature was controlled at 80° C. The molecular size was relative to dextran standards (American Polymer Standards Co., Mentor, Ohio, USA).

Light Microscopy

A drop of sample suspension (1% in water) was deposited on a microscope slide and covered with a cover slip. The sample was observed by an Olympus BX51TF microscope (Olympus Optical Co. Ltd., Shinjuku-ku, Tokyo, Japan). The images in both normal light and polarized light backgrounds were captured using a SPOT 18.2 Color Mosaic camera (Diagnostic Instruments Inc., Sterling Heights, Mich., USA).

Scanning Electron Microscopy (SEM)

The spherulite samples were coated with gold-palladium using a sputter coater (Denton Vacuum, LLC., Moorestown, N.J.) and viewed at 1000× and 4000× magnification with a scanning electron microscope (S-3500N, Hitachi Science Systems, Ltd., Japan) operating at an accelerating voltage of 20 kV.

Wide-Angle X-Ray Diffraction

The crystalline structure of spherulites was studied by wide-angle X-ray diffraction. The experiment was conducted with a Philips X-ray diffractometer with Cu—Ka radiation at 35 kV and 20 mA, a theta-compensating slit, and a diffracted beam monochromator. The moisture of a sample was adjusted to about 15% by storing in a sealed desiccator over water at 25° C. The diffractograms were recorded between 2 and 35° (2θ).

Synchrotron Small-Angle X-Ray Scattering (SAXS)

SAXS experiments were carried out at the Advanced Polymers Beamline (X27C) in the National Synchrotron Light Source, Brookhaven National Laboratory, in Upton, N.Y. The wavelength used was 0.1371 nm and the sample-to-detector distance was 1782.97 mm. A 2D MAR-CCD (Rayonix, LLC, formerly MAR USA, Inc., Evanston, Ill.) X-ray detector was used for data collection. Both samples were examined at an "as is" moisture level and at ~50%. The hydrated sample was mixed with an equal weight of water and the mixture equilibrated at 25° C.

DSC

A spherulite suspension in water (25% solids) was prepared and sealed in a DSC pan and analyzed by DSC (TA Q200 instrument, New Castle, Del., USA). Each sample was heated from 10° C. to 160° C. at 10° C./min. An empty pan was used as a reference. The onset (To), peak (Tp), and conclusion (Tc) temperatures and enthalpy (ΔH) were calculated from the DSC thermogram.

In Vitro Digestion

An in vitro digestion of spherulites was conducted by a modified Englyst procedure. See, Englyst et al., Classification and measurement of nutritionally important starch fractions, *Eur. J. Clin. Nutr.* 1992, 46 (Suppl. 2), 33-50, and Sang et al., Resistant starches from amylose mutants of maize by simultaneous heat-moisture treatment and phosphorylation, *Carbohydr. Polym.* 2006, 63, 167-175, both of which are incorporated by reference herein in their entireties. Samples of the spherulites (~0.6 g) were mixed with guar gum (50 mg) and pepsin (50 mg) in 0.05 M hydrochloric acid (10 mL). Then, sodium acetate solution (0.25 M, 10 mL) and 30 glass beads (~8.4 g) were added. Guar gum (50 mg) in 0.1 M sodium acetate buffer (pH 5.2, 20 mL) and glucose standard solution (20 mL) were used as the blank and standard, respectively. After the enzyme (pancreatin and amyloglucosidase) solution (5 mL) was added, the mixture was shaken in a water bath (Models 25 and 50, Precision, Winchester, Va.) at 37° C. and 90 strokes/min. At 20 min intervals, a 250 μL aliquot of the mixture was taken and added into 66.6% ethanol solution (10 mL). After centrifugation, 100 μL of supernatant was taken, and glucose content was determined by a D-glucose assay procedure with a Megazyme glucose assay kit (Megazyme International Ireland Ltd, Wicklow, Ireland). After 3 h at 37° C., the digestion was stopped by adding 200 mL ethanol. The solids were recovered by filtration and dried in an oven at 40° C. overnight. The in vitro digestion test was repeated once more on the recovered solids.

Results

Molecular Size Distribution and Yield

Figure 1:
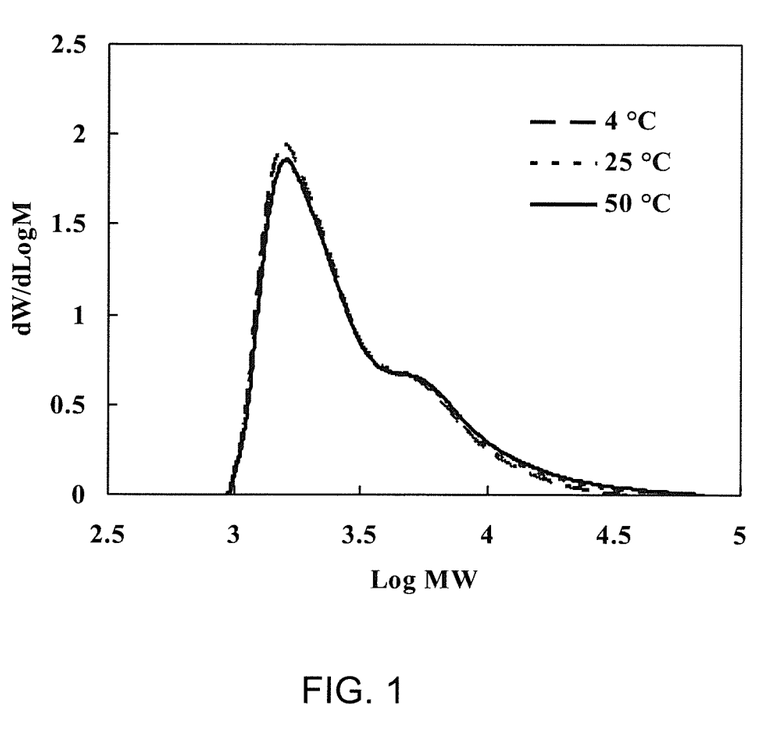
FIG. 1 is a chart showing molecular size distribution of short-chain amylose spherulites produced by heating debranched waxy maize starch (25% w/w) in ~0.06% sodium acetate pH 4 to 180° C. and crystallizing at the different temperatures.

FIG. 1 shows the size distribution of SCA molecules that comprise the spherulites, which was determined by GPC and dextran standards. A bimodal distribution with low and high molecular sizes was observed for the spherulites, and that was anticipated based on data for debranched waxy maize starch. Spherulites that were crystallized at different temperatures had almost identical molecular size distributions. However, spherulites obtained at 4° C. had a slightly larger proportion of the low-molecular size fraction as compared to those produced at 25 and 50° C. This observation suggests that short linear chains associate more at low temperature. The associated molecules crystallized and precipitated from solution. The recovery of SCA spherulites from the 25% SCA solution increased from 50% to 88% as crystallization temperature decreased from 50° C. to 4° C. (see, Table 1). Large-scale production of spherulites appears feasible because of their high yield and recovery by conventional filtration.

TABLE 1

Yield of Short-chain Amylose Spherulites Produced by Heating Debranched Waxy Maize Starch (25% w/w) to 180° C. and Crystallized at Different Temperatures[a]

| Crystallization temperature (° C.) | 4 | 25 | 50 |
|---|---|---|---|
| Yield (%) | 87.6 ± 2.1 | 72 ± 1.4 | 50 ± 1.6 |

[a]Mean ± standard deviation values are reported.

Morphology

Figure 2:
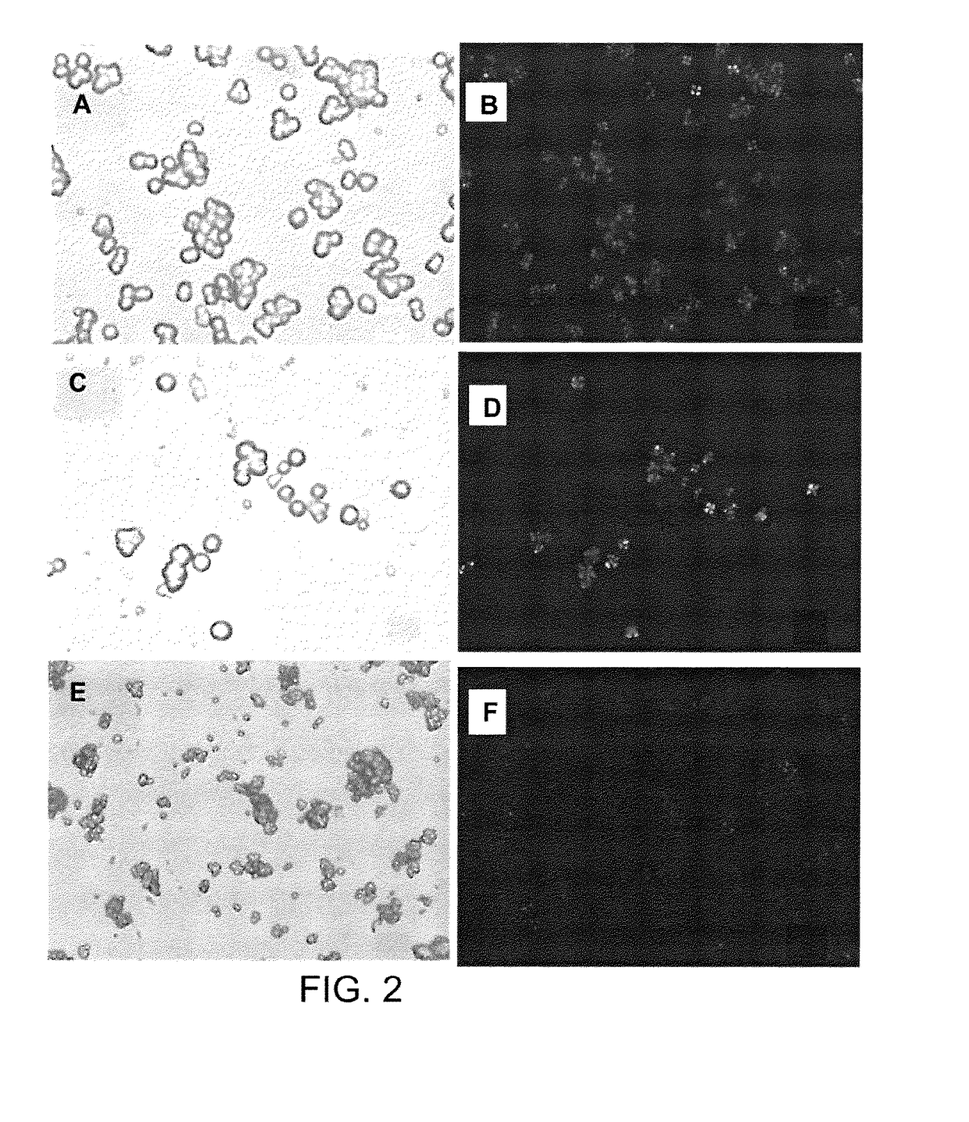
FIG. 2 contains microscopic images of short-chain amylose spherulites produced by heating debranched waxy maize starch (25% w/w) to 180° C. and crystallizing at different temperatures: A and B, 4° C.; C and D, 25° C.; E and F, 50° C.

Microscopic images of SCA spherulites under both normal (left) and polarized (right) light backgrounds are shown in FIG. 2. For materials crystallized at 4° C. (FIGS. 2A and B) and 25° C. (FIGS. 2C and D), birefringence and a Maltese cross were observed under polarized light, confirming the formation of spherulites. The size of the spherulites ranged from 5 to 10 μm. Increasing the crystallization temperature to 50° C. (FIGS. 2E and F) resulted in less well-developed spherulites with a reduced particle size (ca. 1 to 5 μm), and weak birefringence and Maltese cross pattern. Some small spherulites appeared to be fused together, but during the light microscopy experiments, movement of those individual small spherulites was observed. The apparent aggregation of those small spherulites suggested that there was surface adhesion between those spherulites particularly after water was evaporated.

In order to study the optimum heating temperature for forming spherulites, the solution of SCA was heated at 170 and 190° C. for 20 min respectively, and crystallized at 4° C. for 24 h. At both heating temperatures of 170 and 190° C., the spherulites were not well developed. At 170° C., small-size particles of ca. 1 to 5 μm were obtained with weak birefringence, while at 190° C. large particles of ~10 μm formed which were birefringent but without the Maltese cross pattern. Thus, the optimum temperature to preheat SCA at 25% solids for spherulite preparation seems to be 180° C.

Figure 3:
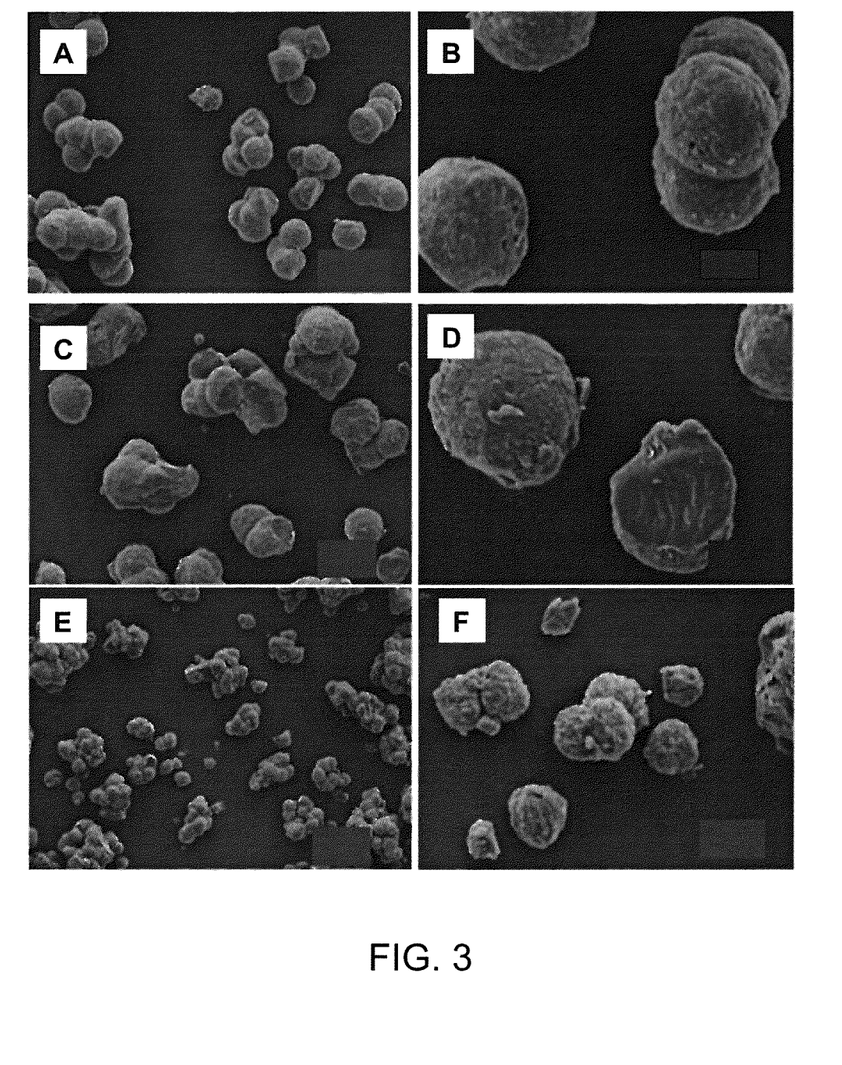
FIG. 3 contains scanning electron microscopic images of short-chain amylose spherulites produced by heating debranched waxy maize starch (25% w/w) to 180° C. and crystallizing at different temperatures: A and B, 4° C.; C and D, 25° C.; E and F, 50° C.

FIG. 3 shows the SEM images of SCA spherulites produced at different crystallization temperatures. A similar morphology and size (ca. 5-10 μm) were found for spherulites formed at 4° C. (FIGS. 3A and B) and 25° C. (FIGS. 3C and D), but spherulites crystallized at 50° C. (FIGS. 3E and F) had a smaller size (ca. 1-5 μm).

Characterization of Crystalline Structure

Figure 4:
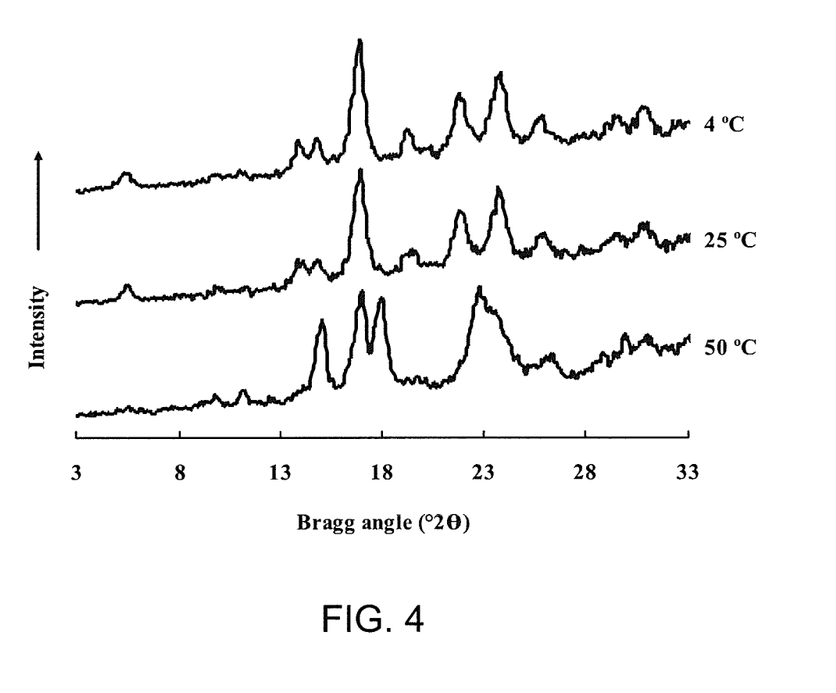
FIG. 4 is a chart showing wide-angle X-ray diffraction of short-chain amylose spherulites produced by heating debranched waxy maize starch (25% w/w) to 180° C. and crystallizing at different temperatures.

The wide-angle X-ray diffraction patterns of spherulites are shown in FIG. 4. Spherulites formed at 4 and 25° C. exhibited the B-type crystallinity, whereas the A-type allomorph was formed at 50° C. The phenomena followed the general rule in SCA crystallization that high temperature favors the formation of A-type crystallites, whereas the reverse condition induces B-type crystallization.

Figure 5:
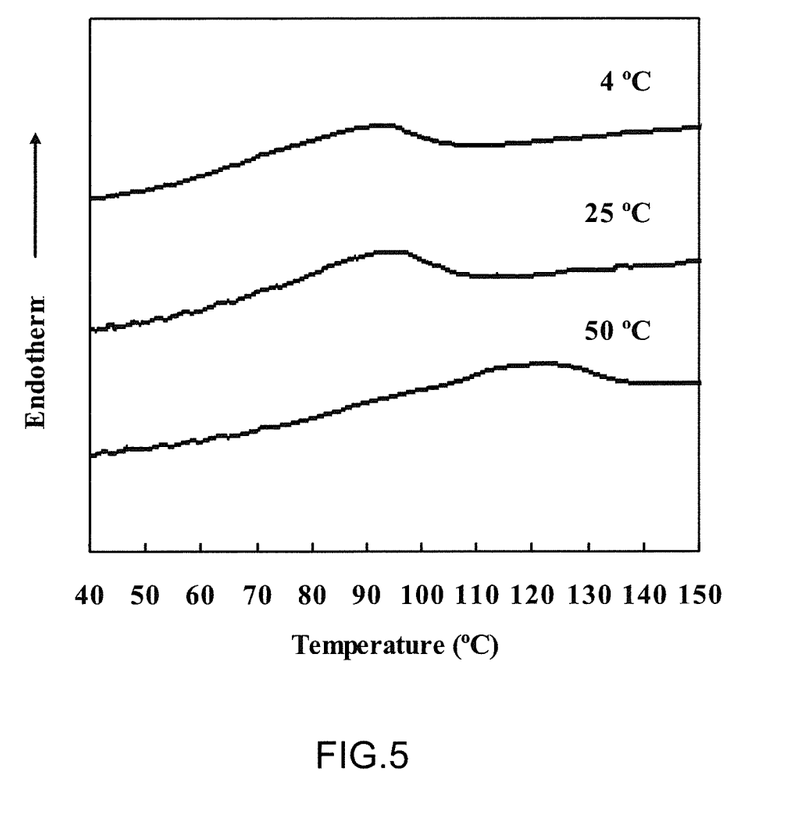
FIG. 5 is a chart showing thermal properties of short-chain amylose spherulites produced by heating debranched waxy maize starch (25% w/w) to 180° C. and crystallizing at different temperatures as determined by differential scanning calorimetry.

The A-type crystalline allomorph of starch is the thermodynamic product, whereas the B-type allomorph results from a kinetic event. See, Gidley, M. J. Factors affecting the crystalline type (AC) of native starches and model compounds—A rationalization of observed effects in terms of polymorphic structures. *Carbohydr. Res.* 1987, 161, 301-304. The melting temperatures of SCA spherulites are largely dependent on their allomorphic form and water content. The thermal properties of spherulites prepared at three different crystallization temperatures are shown in FIG. 5 and Table 2. In excess water, an endothermic peak centered around 90° C. was observed for spherulites obtained at 4 and 25° C., whereas the endotherm of spherulites formed at 50° C. shifted to a higher peak melting temperature of 120° C., indicating that differences in crystallization temperatures can lead to different melting temperatures. In this example, the A-type structure prepared at 50° C. was more thermally stable with a melting temperature about 30° C. higher than the B-type structure obtained at 4 and 25° C.

TABLE 2

Thermal Properties of Short-chain Amylose Spherulites Produced by Heating Debranched Waxy Maize Starch (25% w/w) to 180° C. and Crystallizing at Different Temperatures as Determined by Differential Scanning Calorimetry [a]

| Crystallization temperature (° C.) | To (° C.) | Tp (° C.) | Tc (° C.) | ΔH(J/g) |
|---|---|---|---|---|
| 4 | 64.8 ± 1.2 | 91.4 ± 2.3 | 108.5 ± 0.7 | 20.9 ± 0.1 |
| 25 | 73.5 ± 0.32 | 91.8 ± 1.9 | 109.1 ± 0.9 | 21.0 ± 0.4 |
| 50 | 99.9 ± 1.1 | 117.5 ± 1.9 | 139.1 ± 0.5 | 20.5 ± 0.5 |

[a] Waxy maize starch (25% solids) was debranched and heated to 180° C. and cooled to different crystallization temperatures.

The enthalpy values were similar among the three spherulites prepared at three different crystallization temperatures even though those spherulites had different thermal stabilities as noted by their melting temperatures. The enthalpy value reflects the degree of crystallinity of starch, and in this study, those spherulites had a similar relative degree of crystallinity and were estimated to be 90 to 94%.

No lamellar peak was observed in the SAXS curves of all the spherulite samples with a low moisture content (ca. 5%). For hydrated spherulite samples at ~50% water content, a weak and broad peak was detected for spherulites formed at 4° C., whereas this peak was basically invisible in spherulites formed at 25 and 50° C., suggesting that no regular alternating crystalline and amorphous structure was developed in SCA spherulites, especially at the two higher crystallization temperatures. These results suggest that even though spherulites produced in this study were birefringent and had a Maltese cross, the organization of the molecules were different from those in native starch. For hydrated native starch granules, a narrow 9 nm lamellar peak is observed by SAXS, which is attributed to a repeating structure of alternating amorphous and crystalline regions. It is possible that the chain length of SCA is too short and irregular in length to form partially crystalline particles with repeating distance between highly packed double helices and poorly packed irregular zones. Thus, no long length scale-order beyond the crystal packing of double helices was observed by SAXS, as is the case for the native starch. However, at the low crystalline temperature of 4° C., a weak broad peak ranging from ca. 0.3 to 1.2 $nm^{-1}$ was observed, suggesting that some SCA molecules transversed double helical crystals to form regions of low density.

It is worth comparing the SAXS results in this study with previous studies on acid hydrolyzed starches. See, e.g., Jenkins, P.; Donand, M. A., The effect of acid hydrolysis on native starch granule structure. Starch/Stärke 1997, 49, 262-267; and Wang, S.; Blazek, J.; Gilbert, E.; Copeland, L., New insights on the mechanism of acid degradation of pea starch. *Carbohydr. Polym.* 2012, 87, 1941-1949. After amorphous regions in starches had been extensively removed by acid, the intensity of the SAXS lamellar peak was reduced. This reduction in SAXS peak seems to be consistent with the SAXS results in this study. The interconnected crystalline and amorphous regions were no longer in place after the waxy maize starch granules were cooked and debranched. Instead, the short linear chains that were released became well aligned during the crystallization and they formed double helices and strong crystallites.

Figure 6:
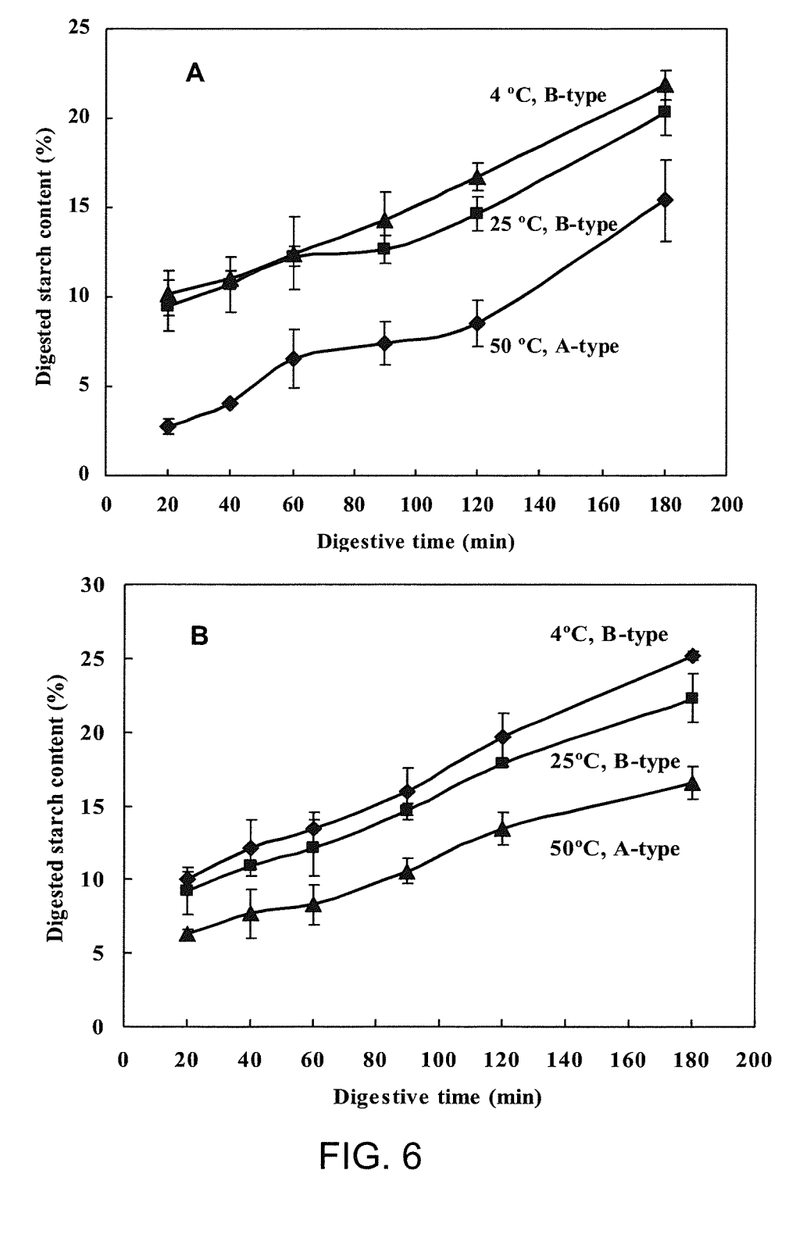
FIG. 6 In vitro digestion profile of (A) short-chain amylose spherulites produced by heating debranched waxy maize starch (25% w/w) to 180° C. and crystallizing at different temperatures, and (B) their digestive residues.

In Vitro Digestion Profile (FIG. 6)

The spherulites prepared at 50° C., which had an A-type X-ray diffraction pattern (FIG. 4), showed the lowest digestibility among the three spherulites crystallized at different temperatures (FIG. 6A) even though the spherulites crystallized at 50° C. had the smallest particle size (FIGS. 2 and 3). Only 15.4% of the spherulites were digested after 3 h. The spherulites formed at 4 and 25° C. gave a B-type X-ray pattern (FIG. 4) with a larger particle size, and they were digested in 3 h to an extent of 20.4% and 21.9%, respectively. One remarkable feature of the digestion curve of the spherulites formed at 4° C. was that the rate was essentially linear as a function of digestion time between 20 min and 3 h (FIG. 6A). The digestion test was repeated once more on the recovered undigested solids. Digestion profiles of the undigested residues showed similarly linear digestive pattern as the parent spherulites (FIG. 6B), demonstrating that the spherulites were digested at essentially a constant rate between 20 min and 3 h. The residues from the first digestion of spherulites that had been formed at 50° C. were again more enzyme resistant than those that had formed at 4 and 25° C. A slight increase in digestion was observed for all the digestive residues after 3 h of the second digestion (FIG. 6B) as compared to their parent counterparts (FIG. 6A), which may be attributed to an altered morphology or structure in the residues after the first digestion.

Figure 7:
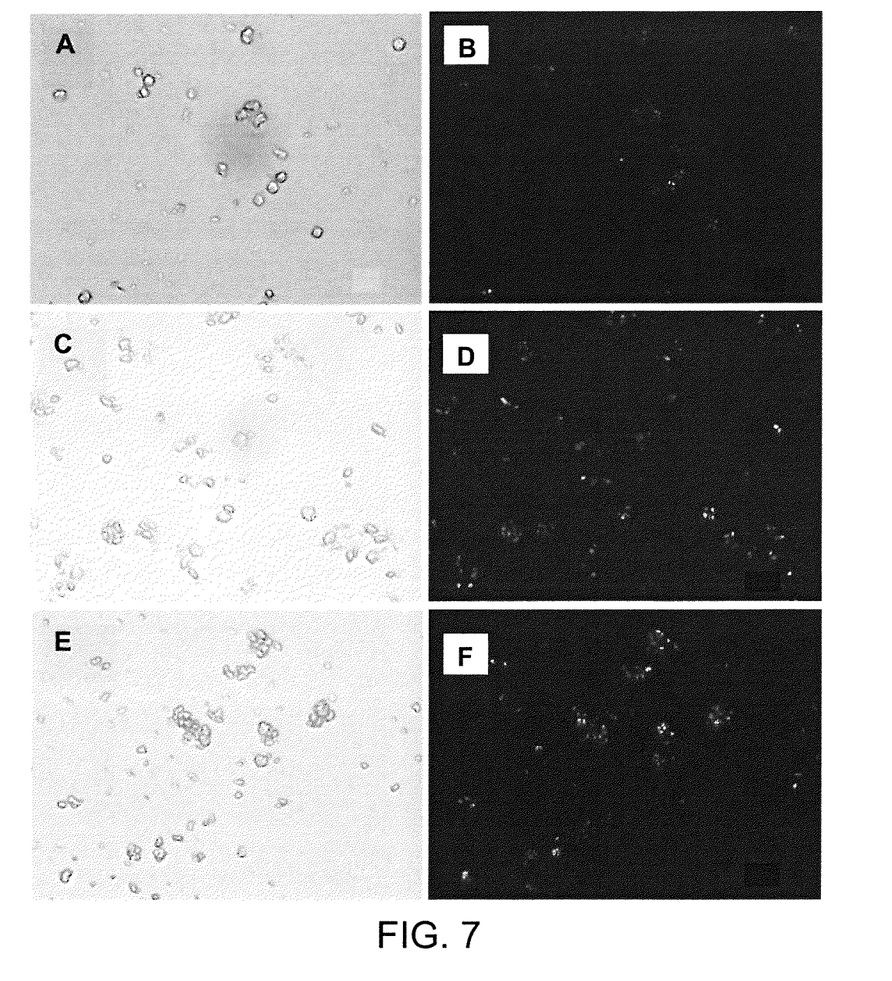
FIG. 7 contains microscopic images of digestive residues from short-chain amylose spherulites produced by heating debranched waxy maize starch (25% w/w) to 180° C. and crystallizing at different temperatures: A and B, 4° C.; C and D, 25° C.; E and F, 50° C.
Figure 8:
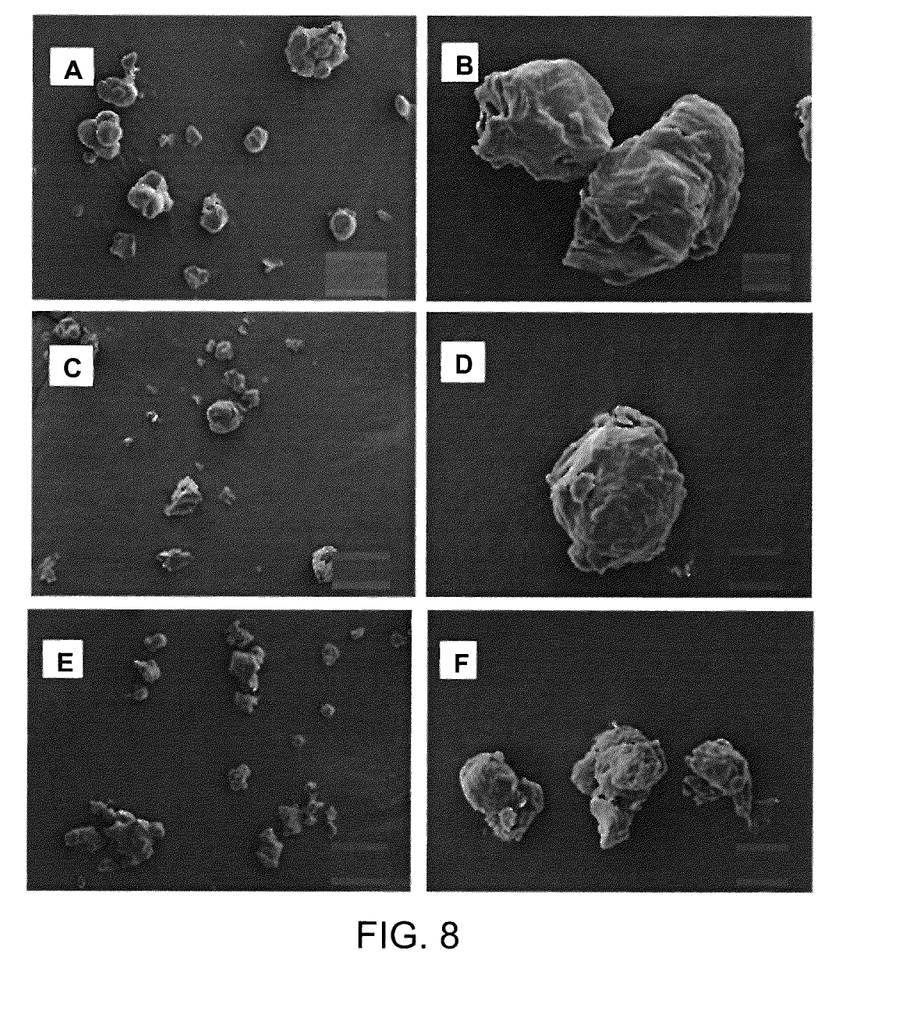
FIG. 8 contains scanning electron microscopic images of digestive residues from short-chain amylose spherulites produced by heating debranched waxy maize starch (25% w/w) to 180° C. and crystallizing at different temperatures: A and B, 4° C.; C and D, 25° C.; E and F, 50° C.

To further understand the digestion mechanism, light microscopy was used to examine the residues of spherulites after the second digestion step (FIG. 7). FIGS. 7A and B represent those spherulites formed at 4° C.; FIGS. 7C and D represent those spherulites formed at 25° C.; and FIGS. 7E and F represent those spherulites formed at 50° C. The residues still contained intact spherulites with a clear Maltese cross along with small pieces of fragmented spherulites. These results suggest that enzyme hydrolysis was not homogenous and that some spherulites were completely hydrolyzed whereas other spherulites remained birefringent. In general, the particle size appeared to be smaller after digestion, particularly for the B-type spherulites. SEM data (FIG. 8) showed a rough surface structure for all the digestion residues of spherulites, indicating that surface erosion rather than the endo-corrosion had occurred during starch digestion. FIGS. 8A and B represent those spherulites formed at 4° C.; FIGS. 8C and D represent those spherulites formed at 25° C.; and FIGS. 8E and F represent those spherulites formed at 50° C. It is known that the enzymatic degradation of native starch granules is not homogeneous. The enzymes enlarge holes occurring as weak points on a granule's surface. Those holes lead to channels inside the granules, which are the path for enzymes to access the less resistant regions near the hilum in a granule. In contrast, no holes or pores were observed in this study during digestion of the spherulites by the mixtures of α-amylase and glucoamylse.

The rate of enzyme hydrolysis or the digestion curve of starch is dependent on the level of enzyme activity. The linear rate of digestion observed (FIG. 6) seems to suggest that the enzyme hydrolysis proceeded on one spherulite at the time, or had a mode of "single spherulite attack" as opposed to "multi spherulite attack". Microscopic data (FIGS. 2 and 7) suggested that the enzyme hydrolysis was not homogenous.

Discussion

Formation of Spherulites from SCA

Figure 9:
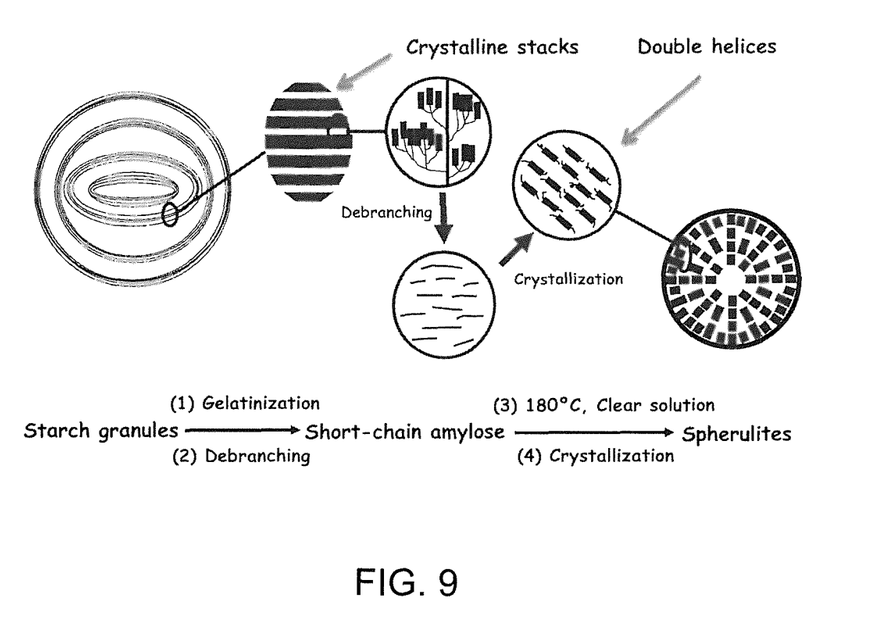
FIG. 9 is a schematic drawing of transition from short-linear chains generated from debranching of waxy maize starch into spherulites.

Amylose is known to be the effective starch component that induces the formation of spherulites. In this study, short, complete linear chains obtained from debranched waxy maize starch were used to prepare spherulites. FIG. 9 is a schematic drawing of the transitions of SCA from starch granules to SCA spherulites. Native starch granules are proposed to contain an amorphous background interrupted by semi-crystalline growth rings that are comprised of regularly repeating crystalline and amorphous lamella. After being cooked in water at a high temperature, the crystalline structure of the starch granule was destroyed, allowing branch points to be cleaved by isoamylase and producing completely linear chains.

Upon debranching 25% waxy maize starch with isoamylase at 50° C., the liquid reaction mixture appeared opaque. However, the mixture was converted to a clear solution after it was heated to 140° C. When the solution was cooled from this temperature (or the temperature range of 140-180° C.), aggregates of particles with irregular shapes were observed. Those materials showed week birefringence and a sharp wide-angle X-ray diffraction pattern, confirming the formation of double helices and a crystalline structure. But, the Maltese cross was not observed in these particles under polarized light, suggesting that the double helices were not radially orientated. Interestingly, when the solution of SCA was cooled from 180° C., a weak lamellar structure was formed as evidenced by the broad peak detected in SAXS curves of the hydrated spherulites.

The production of spherulite crystals of amylose from aqueous solution depends on the relative rates of phase separation and polymer association (crystallization). It is only when phase separation is induced well before the nucleation of crystallization that the formation of spherulites occurs. At the temperature of 180° C., the molecules in the SCA solution shifted in conformation from helix to coil state, and the solution separated into a polymer-poor and polymer-rich phase at ~140-180° C. Upon further cooling, the double helices formed in the polymer-rich phase became self-aligned into crystalline arrangement, which grew into spherulites that precipitated from the liquid medium. Thus, spherulite formation from SCA appeared to involve a conformational transition from coils to double helices, alignment of double helices into bundles that crystallized with limited amorphous loose ends, and radial orientation of the bundles into spherulites (FIG. 9). Spherulites can be classified by their fiber density. The spherulites formed from SCA in this study appear to be compact and do not contain free space between individual crystallites. It is postulated that the spherulites from SCA grew radially from the nucleation site and formed via central multidirectional growth.

Digestibility of A- and B-Type Spherulites

The results of the present study show that it is possible to produce spherulites with the A-type crystallinity that are more resistant to enzymatic hydrolysis than the B-type (see, FIG. 6). In the present work, the A- and B-spherulites were comprised of only linear chains, and both types had similar molecular size distribution (see, FIG. 1). The A- and B-type spherulites in the present study displayed a radial orientation of molecules (birefringence with Maltese cross) and similar surface smoothness (FIGS. 2 and 3), although the Maltese cross was not well observed in A-type spherulites due to their small particle size.

In this study, the spherulite size was not correlated with the digestibility. The A-type spherulite had a smaller particle size (larger surface area) than the two other B-type spherulites (see, FIG. 3) but the A-type was still more enzyme-resistant (see, FIG. 6). Moreover, the A-type spherulite had the highest melting temperature (see, Table 2, and FIG. 5), indicating it contained strong crystallites, i.e. tighter packing of its double helices. The B-type spherulite was more susceptible to α-amylase/amyloglucosidase hydrolysis than the A-type spherulite (FIG. 6). This observation is in striking contrast to prior findings that native starch granules with a B-type X-ray pattern are more amylase-resistant than those with an A-type X-ray pattern. The denser structure in the A-type spherulites most likely inhibited the access of enzymes to starch molecules and led to their lower digestibility compared to the B-type.

In conclusion, a novel high yield process combining enzymatic debranching, melting and crystallization was developed to convert waxy maize starch at high solids (~25%) to spherulites with a high melting temperature and a controlled enzyme digestibility. When the spherulites were digested by a mixture of α-amylase and amyloglucosidase, solids were lost at essentially a constant rate up to ~25%. The A-type spherulites had a smaller particle size (1-5 μm) but were still more resistant to enzyme digestion than the B-type spherulites (5-10 μm). The results of this study suggested that size or surface area is not a determining factor controlling the digestibility of spherulites. As reflected in their greater thermal stability, the organization of A-type crystallites seemed to be more compact and stronger than that of B-type crystallites and therefore was more resistant to enzyme digestion.

We claim:

1. A method of producing spherulites comprising linear α-1,4-linked glucans, said method comprising:
   (i) forming an aqueous slurry comprising from 15% to about 50% by weight of a waxy starch material having an amylopectin content of greater than 50% by weight;
   (ii) cooking said starch material by heating said aqueous slurry to a temperature of 110° C. to about 150° C. for 5 minutes to about 2 hours, thereby destroying the crystalline structure of said starch material and forming a cooked starch slurry;
   (iii) cooling said cooked starch slurry to a temperature of 35° C. to 75° C., thereby forming a cooled starch slurry;
   (iv) treating said cooled starch slurry with one or more enzymes capable of hydrolyzing alpha-1,6 linkages within amylopectin thereby causing debranching of said starch material and resulting in the creation of a debranched starch mixture having greater than 50% α-1,4-linked glucans by weight based upon the total starch weight;
   (v) heating said debranched starch mixture to a temperature above the melting point of the starch contained therein and within the range of 160° C. to 210° C., thereby melting the starch contained in the debranched starch mixture and forming a melted starch mixture; and
   (vi) either:
      (a) cooling said melted starch mixture to a temperature of greater than 25° C. to 75° C. thereby crystallizing said spherulites, said spherulites having predominantly A-type crystallinity and an average particle size of 1 to 5 μm; or
      (b) cooling said melted starch mixture to a temperature of from 0° C. to 25° C. thereby crystallizing the starch into said spherulites, said spherulites having predominantly B-type crystallinity and an average particle size of 5 to 10 μm.

2. The method according to claim 1, wherein said enzyme treatment step results in said starch mixture having greater than 90% α-1,4-linked glucans by weight based upon the total starch weight.

3. The method according to claim 1, wherein said one or more enzymes comprise isoamylase or pullulanase.

4. The method according to claim 1, wherein said spherulites have melting point of between about 80° C. to about 160° C.

5. The method according to claim 1, wherein said spherulites are resistant to enzyme digestion, exhibiting less than 30% digestion when exposed to an α-amylase-containing solution for 3 hours at 37° C.

6. The method according to claim 1, wherein said waxy starch material has an amylopectin content of greater than 90% by weight.

7. The method according to claim 1, wherein said debranched starch mixture comprises short-chain amylose (SCA).

8. The method according to claim 1, wherein said spherulites comprise amylose molecules having an average molecular weight of less than 200,000.

9. The method according to claim 1, wherein said spherulites comprise amylose molecules have a degree of polymerization of between about 10 to about 100.

10. The method of claim 1, wherein said aqueous slurry comprises from about 25% to about 40% by weight of said waxy starch material.

* * * * *